United States Patent [19]
Inturrisi

[11] Patent Number: 6,008,258
[45] Date of Patent: Dec. 28, 1999

[54] D-METHADONE, A NONOPIOID ANALEGESIC

[75] Inventor: Charles E. Inturrisi, Torrington, Conn.

[73] Assignee: Cornell Research Foundation, Inc., Ithaca, N.Y.

[21] Appl. No.: 09/010,239

[22] Filed: Jan. 21, 1998

Related U.S. Application Data

[60] Provisional application No. 60/035,308, Jan. 22, 1997.

[51] Int. Cl.$^6$ .......................... A01N 33/02; A61K 31/135
[52] U.S. Cl. ............................................. 514/648; 514/812
[58] Field of Search ...................... 514/648, 812

[56] References Cited

U.S. PATENT DOCUMENTS

| | | | |
|---|---|---|---|
| 3,895,056 | 7/1975 | Billings et al. | 260/490 |
| 5,321,012 | 6/1994 | Mayer et al. | 514/25 |
| 5,352,683 | 10/1994 | Mayer et al. | 514/289 |
| 5,502,058 | 3/1996 | Mayer et al. | 514/289 |
| 5,556,838 | 9/1996 | Mayer et al. | 514/25 |
| 5,654,281 | 8/1997 | Mayer et al. | 514/25 |

OTHER PUBLICATIONS

Olsen et al.: Clinical Effects and Pharmacokinetics of Racemic Methdone and Its Optical Isomers, 1977, 147–57, see entire abstract.

Kristensen et al: Stereoselective Pharmacokinetics of Methadone in Chronic Pain Patients, 1996, 221–227, see entire abstract.

Choi et al: Opioids and Non–Opioid Enantiomers Selectively Attenuate NMDA Neurotoxicity on Cortical Neurons, 27–35, see entire abstract.

*Primary Examiner*—Frederick Krass
*Attorney, Agent, or Firm*—Nixon Peabody LLP

[57] ABSTRACT

The present invention relates to a method of treating pain in a subject having a NMDA recptor which includes administering d-methadone, d-methadol, d-alpha-acetylmethadol, l-alpha-acetylmethadol, d-alpha-normethadol, l-alpha-normethadol, pharmaceutically acceptable salts thereof, or mixtures thereof, to the subject under conditions effective for the substance to bind to the NMDA receptor of the subject. The present invention further relates to a method of treating tolerance and physical dependence in a subject and a method of binding to a NMDA receptor.

20 Claims, 5 Drawing Sheets

D-METHADONE, A NONOPIOID ANALEGESIC

This application claims the benefit of U.S. Provisional Patent Application Ser. No. 60/035,308, filed Jan. 22, 1997, which is hereby incorporated by reference.

This invention was developed with government funding under National Institute on Drug Abuse Nos. DA01457, DA07274, DA00255, and DA00198. The U.S. Government may have certain rights.

FIELD OF THE INVENTION

The present invention relates to a method of treating pain, and the tolerance and physical dependence associated with the repeated use of opioids for pain, using d-methadone. In addition, the present invention relates to a method of treating the tolerance, physical dependence, and/or craving associated with narcotic addition, using d-methadone.

BACKGROUND OF THE INVENTION

Tolerance and physical dependence are predictable consequences of the chronic administration of morphine and morphine-like opioids. These pharmacological properties of opioids are undesirable for both the opioid addict and the pain patient. In the opioid addict, tolerance to the mood effects of an opioid results in rapid dose escalation. Further, withdrawal is a powerful stimulus, engendering drug seeking behavior. For the pain patient, tolerance to opioid analgesia necessitates dose escalation, which can result in an increase in adverse effects (Inturrisi, C.E. "Opioid Analgesic Therapy in Cancer Pain," *Advances in Pain Research and Therapy*, (K. M. Foley, J. J. Bonica, and V. Ventafridda, Eds.) pp. 133–154, Raven Press, New York (1990) ("Inturrisi")). The development of physical dependence exposes both the pain patient and the opioid addict to the risk of the withdrawal syndrome if opioid administration is abruptly discontinued or an opioid antagonist is inadvertently administered (Inturrisi). Thus, nonopioid drugs that could attenuate and/or reverse opioid tolerance and physical dependence would be a usefull adjunct in pain management. These same drugs could be used in the opioid addict to assist in opioid detoxification and during maintenance treatment by reducing or eliminating withdrawal symptoms. Furthermore, nonopioid drugs that modulate tolerance and dependence, without altering the analgesia effects of opioids, could provide an important new tool with which to investigate the biochemical and molecular mechanisms of opioid analgesia, craving, tolerance, and physical dependence. Thus, a strong argument can be made for the preclinical pharmacological evaluation of nonopioid modulators of opioid tolerance and/or dependence in both "analgesic" and "drug abuse" model systems.

Recent studies (Trujillo et al., "Inhibition of Morphine Tolerance and Dependence by the NMDA Receptor Antagonist MK-801," *Science*, 251:85–7 (1991) ("Trujillo"); Marek et al., "Excitatory Amino Acid Antagonists (Kynurenic Acid and MK-801) Attenuate the Development of Morphine Tolerance in the Rat," *Brain Res.*, 547:77–81 (1991); Tiseo et al., "Attenuation and Reversal of Morphine Tolerance by the Competitive N-methyl-D-aspartate Receptor Antagonist, LY274614," *J. Pharmacol. Exp. Ther.*, 264:1090–96 (1993) ("Tiseo I"); Kolesnikov et al., "Blockade of mu and kappa$_1$ Opioid Analgesic Tolerance by NPC 177442, a Novel NMDA antagonist," *Life Sci.*, 53:1489–94 (1993); Kolesnikov et al., "Blockade of Tolerance to Morphine but not to κ Opioids by a Nitric oxide Synthase Inhibitor," *Proc. Natl. Acad. Sci. USA*, 90:5162–66 (1993); Tiseo et al., "Modulation of Morphine Tolerance by the Competitive N-methyl-D-aspartate Receptor Antagonist LY274614: Assessment of Opioid Receptor Changes," *J. Pharmacol. Exp. Ther.*, 268:195–201 (1994) ("Tiseo II"); Elliott et al., "The NMDA Receptor Antagonists, LY274614 and MK-801, and the Nitric Oxide Synthase Inhibitor, NG-Nitro-L-arginine, Attenuate Analgesic Tolerance to the Mu-Opioid Morphine but not to Kappa Opioids," *Pain*, 56:69–75 (1994) ("Elliott I"); Elliott et al., "Dextromethorphan Attenuates and Reverses Analgesic Tolerance to Morphine," *Pain*, 59:361–368 (1994) ("Elliott II"); Inturrisi, C.E., "NMDA Receptors, Nitric Oxide, and Opioid Tolerance," *Reg. Peptides*, 54:129–30 (1994) have demonstrated that the excitatory amino acid ("EAA") receptor system and the nitric oxide ("NO") system are involved in morphine tolerance and dependence. Since the 1980s, EAAs including glutamate and aspartate, have been identified as neurotransmitters in the vertebrate central nervous system ("CNS"). An important aspect of one EAA, N-methyl-D-aspartate ("NMDA"), is that it opens a distinctive membrane channel, characterized by voltage dependent $Mg^{2+}$ blockade and high permeability to calcium ions. Physiologic increases in intracellular calcium subsequent to receptor activation can initiate a number of metabolic changes in the cell, including a calcium-calmodulin mediated activation of nitric oxide synthase ("NOS") leading to the production of NO (Bredt et al., "Nitric Oxide a Novel Neuronal Messenger," *Neuron*, 8:3–11 (1992)). Activation of NMDA receptors can also alter the expression of cellular regulatory genes, such as c-fos (Bading et al., "Regulation of Gene Expression in Hippocampal Neurons by Distinct Calcium Signaling Pathways," *Science*, 260:181–86 (1993); Rasmussen et al., "NMDA Antagonists and Clonidine Block C-fos Expression During Morphine Withdrawal," *Synapse*, 20:68–74 (1995)). However, large and prolonged increases in intracellular calcium, such as those which can occur from excessive NMDA receptor stimulation, are toxic to the cell. Stimulation of EAA/NMDA receptors may represent the pathophysiologic basis of neuronal degeneration in acute or chronic conditions (Meldrum et al., "Excitatory Amino Acid Neurotoxicity and Neurodegenerative Disease," In Lodge D, Collingridge L (eds), *Trends in Pharmacological Sciences: The Pharmacology of Excitatory Amino Acids A Special Report*, Cambridge, UK, Elsevier, pp. 54–62 (1991)). Thus, EAA receptor antagonists, especially NMDA receptor antagonists, represent a major area of drug development.

In particular, recent studies have demonstrated that co-administration of NMDA receptor antagonists attenuate or reverse the development of tolerance to the analgesic effects of morphine in rodents (Marek, et al., "Delayed Application of MK-801 Attenuates Development of Morphine Tolerance in the Rat," *Brain Res.*, 548:77–81 (1991) ("Marek"); Trujillo; Tiseo I; Tiseo II, Elliott I; Elliott II). Marek discusses the role of MK-801, an NMDA receptor antagonist or blocker, in reducing morphine dependence in laboratory animals. However, MK-801 has been found to be toxic and is, therefore, unsuitable for pharmaceutical use. NMDA receptor antagonists that are currently available for clinical use include ketamine, dextromethorphan, and memantine. Ketamine's utility is limited, because it is only available for use by injection and commonly produces profound psychotomimetic and other undesirable effects at doses required for analgesic effects. Dextromethorphan's utility is limited, because patients with a genetically determined absence of cytochrome P-4502D6 (the liver drug metabolizing enzyme) cannot tolerate increases in dosage.

Dextromethorphan is also subject to drug-drug interactions with commonly used drugs that may affect its efficacy and side effect profile. Further, dextromethorphan is rapidly eliminated form the body, necessitating frequent administration. Memantine, a drug used for movement disorders, is currently under clinical investigation and its therapeutic ratio remains to be determined.

Like morphine, methadone binds preferentially to the mu-type of the opioid receptor (Neil, A., "Affinities of Some Common Opioid Analgesics Towards Four Binding Sites in Mouse Brain," *Naunvn-Schmiedeberg's Arch. Pharmacol.*, 328:24–9 (1984)), and produces behavioral effects similar to morphine in rodents and humans (Olsen, G. D., et al. "Clinical Effects and Pharmacokinetics of Racemic Methadone and its Optional Isomers," *Clin. Pharmacol. Ther.*, 21:147–157 (1976) ("Olsen"); Smits et al., "Some Comparative Effects of Racemic Methadone and Its Optical Isomers in Rodents," *Res. Commun. Chem. Pathol Pharmacol.*, 7:651–662 (1974) ("Smits")). The clinically available and commonly used form of methadone is as the racemic mixture (d,l-methadone). The l-isomer is responsible for the opioid properties, whereas the d-isomer is weak or inactive as an opioid (Horng et al., "The Binding of the Optical Isomers of Methadone, α-Methadol, A-Acetylmethadol and Their N-demethylated Derivatives to the Opiate Receptors of Rat Brain," *Res. Commmun. Chem. Pathol. Pharmacol.*, 14:621–29 (1976) ("Horng")). d-Methadone does not produce opioid-like locomotor activity in mice (Smits), is inactive following intraventricular administration in rats (Ingoglia et al., "Localization of d- and l-methadone after Intraventricular Injection into Rat Brain," *J. Pharmacol. Exp. Ther.*, 175:84–87 (1970)), and is a 50-fold less potent analgesic in humans than l-methadone (Olsen). Further, l-methadone has a 30-fold greater ability to displace [$^3$H]naloxone binding than d-methadone (Horng). Thus, the opioid analgesic properties of dl-methadone are attributed to l-methadone (Olsen). The use of d-methadone has not been investigated.

The present invention is directed to overcoming these deficiencies.

BRIEF DESCRIPTION OF THE DRAWINGS

FIGS. 4A–B show intrathecal (IT) d-methadone dose-dependently reduces formalin-induced flinching behavior during phase 2 of the formalin response. d-Methadone at an IT dose of 32, 160, or 320 μg/rat, or saline (0 μg/rat), was administered to rats 15 minutes before the intraplantar injection of 50 μl of 5% formalin.

SUMMARY OF THE INVENTION

The present invention relates to a method of treating pain in a subject having a NMDA receptor which includes administering a substance selected from the group consisting of d-methadone, d-methadol, d-alpha-acetylmethadol, l-alpha-acetylmethadol, d-alpha-normethadol, l-alpha-normethadol, pharmaceutically acceptable salts thereof, and mixtures thereof, to the subject under conditions effective for the substance to bind to the NMDA receptor of the subject. The substance can be used alone or in combination with other pain relieving substances.

Another aspect of the present invention relates to a method of treating addiction to a narcotic analgesic or addictive substance in a subject having a NMDA receptor which includes administering a substance selected from the group consisting of d-methadone, d-methadol, d-alpha-acetylmethadol, l-alpha-acetylmethadol, d-alpha-normethadol, l-alpha-normethadol, pharmaceutically acceptable salts thereof, and mixtures thereof, to the subject under conditions effective for the substance to bind to the NMDA receptor of the subject.

Yet another aspect of the present invention relates to a method of blocking a NMDA receptor which includes contacting the NMDA receptor with a substance selected from the group consisting of d-methadone, d-methadol, d-alpha-acetylmethadol, l-alpha-acetylmethadol, d-alpha-normethadol, l-alpha-normethadol, pharmaceutically acceptable salts thereof, and mixtures thereof, to the subject under conditions effective for the substance to bind to and block the NMDA receptor.

The present invention provides for a safe and effective treatment for pain and narcotic tolerance and physical dependence. d-methadone is not subject to the genetic or drug interactions of dextromethorphan, nor does it appear to produce psychotomimetic effects. Further, d-methadone, when used as part of a racemic mixture, has a long history of safety. Also d-methadone has a much longer elimination half-life (approximately 24 hours) than the other clinically available NMDA receptor antagonists. Therefore, d-methadone can be used in combination with the longer acting forms of opioids, such as morphine or oxycodone, to provide a convenient once or twice a day dosing schedule.

DETAILED DESCRIPTION OF THE INVENTION

The present invention relates to a method of treating pain in a subject having a NMDA receptor which includes administering a substance selected from the group consisting of d-methadone, d-methadol, d-alpha-acetylmethadol, l-alpha-acetylmethadol, d-alpha-normethadol, l-alpha-normethadol, pharmaceutically acceptable salts thereof, and mixtures thereof, to the subject under conditions effective for the substance to bind to the NMDA receptor of the subject. The substance can be used alone or in combination with other pain relieving substances.

Another aspect of the present invention relates to a method of treating addiction to a narcotic analgesic or addictive substance in a subject having a NMDA receptor which includes administering a substance selected from the group consisting of d-methadone, d-methadol, d-alpha-acetylmethadol, l-alpha-acetylmethadol, d-alpha-normethadol, l-alpha-normethadol, pharmaceutically acceptable salts thereof, and mixtures thereof, to the subject under conditions effective for the substance to bind to the NMDA receptor of the subject.

Yet another aspect of the present invention relates to a method of blocking a NMDA receptor which includes contacting the NMDA receptor with a substance selected from the group consisting of d-methadone, d-methadol, d-alpha-acetylmethadol, l-alpha-acetylmethadol, d-alpha-normethadol, l-alpha-normethadol, pharmaceutically acceptable salts thereof, and mixtures thereof, to the subject under conditions effective for the substance to bind to and block the NMDA receptor.

The subject invention is best understood through a discussion of receptors and signal transduction pathways. Cells in higher animals normally communicate by means of hundreds of kinds of extracellular signaling molecules, including proteins, small peptides, amino acids, nucleotides, steroids, retinoids, fatty acid derivatives, and even dissolved gases, such as nitric oxide and carbon monoxide. These signaling molecules relay a "signal" to another cell (a "target cell"), generally affecting a cellular function. Receptors for extracellular signaling molecules are collectively referred to as "cell signaling receptors".

Many cell signaling receptors are transmembrane proteins on a cell surface; when they bind an extracellular signaling molecule (a ligand), they become activated to generate a cascade of intracellular signals that alter the behavior of the cell. In contrast, in some cases, the receptors are inside the cell and the signaling ligand has to enter the cell to activate them; these signaling molecules therefore must be sufficiently small and hydrophobic to diffuse across the plasma membrane of the cell.

In addition to ligand binding to the receptors, the receptors can be blocked to prevent ligand binding. When a substance binds to a receptor, the three-dimensional structure of the substance fits into a space created by the three-dimensional structure of the receptor in a ball and socket configuration. The better the ball fits into the socket, the more tightly it is held. This phenomenon is called affinity. If the affinity of a substance is greater than the original ligand, it will compete with the ligand and bind the binding site more frequently. Once bound, signals may be sent through the receptor into the cells, causing the cell to respond in some fashion. This is called activation. On activation, the activated receptor then directly regulates the transcription of specific genes. But the substance and the receptor must have certain attributes, other than affinity, in order to activate the cell. Chemical bonds between atoms of the substance and the atoms of the receptors must form. In some cases, this leads to a slight change in the configuration of the receptor which is enough to begin the activation process (called signal transduction). As a result, substances can be made which bind receptors and activate them (called receptor agonists) or inactivate them (called receptor antagonists).

The N-methyl-D-aspartate ("NMDA") receptor complex has important roles in numerous central nervous system ("CNS") processes, including memory and long-term potentiation, regulation of neuronal degeneration, and protection against excitotoxic injury (Monaghan et al., "The Excitatory Amino Acid Receptors: Their Classes, Pharmacology, and Distinct Properties in the Function of the Central Nervous System," *Annu. Rev. Pharmacol. Toxicol.*, 29:365–402 (1989), which is hereby incorporated by reference). NMDA receptors also appear to be involved in the processing of nociceptive information (Dickenson, A. H., et al. "Dextromethorphan and Levorphanol are Dorsal Horn Nociceptive Neurones in the Rat," *Neuropharmacology*, 30:1303–1308 (1991)). Additionally, previous studies have shown that NMDA receptor antagonists attenuate and reverse the development of tolerance to the mu-opioid morphine without altering morphine's analgesic properties (Elliott et al., "N-methyl-D-aspartate (NMDA) Receptors Mu and Kappa Opioid Tolerance, and Perspectives on New Analgesic Drug Development," *Neuropsychopharmacology*, 13:347–356 (1995), which is hereby incorporated by reference).

Ebert, et al., "Ketobemidone, Methadone, and Pethidine are Non-Competitive Antagonists in the Rat Cortex and Spinal Cord," *Neurosci. Lett.*, 187:165–68 (1995), which is hereby incorporated by reference, have reported that racemic methadone possesses low $\mu$m affinity for the NMDA receptor in rat cortical membranes, and reduces NMDA-induced depolarization in vitro in rat spinal cord and cortical wedge preparations. In contrast to this finding, the present invention has identified that both the d- and l-isomers of methadone can bind to the noncompetitive (MK-801) site on the NMDA receptor (Gorman et al., "The d- and l-Isomers of Methadone Bind to the Non-Competitive Site on the N-methyl-D-aspartate (NMDA) Receptor in Rat Forebrain and Spinal Cord," *Neurosci. Lett.*, 223:5–8 (1997), which is hereby incorporated by reference) in rat forebrain and spinal cord membranes with an affinity approximately equal to that of dextromethorphan, an established NMDA receptor antagonist (Elliott, et al., "Dextromethorphan Suppresses Both Formalin-Induced Nociceptive Behavior and the Formalin-Induced Increase in Spinal Cord c-fos mRNA," *Pain*, 61:401–09 (1995), which is hereby incorporated by reference). Although not meaning to be bound by theory, it is believed that d-methadone functions in a similar manner to treat pain and to treat the physical dependence on and tolerance to a narcotic substance.

Thus, d-methadone, when supplied to a subject in an effective amount, can bind to and block a NMDA receptor of the subject. Preferably, the NMDA receptor is located in the central and peripheral nervous systems. The central nervous system includes the brain and the spinal cord, while the peripheral nervous system includes sensory neurons (peripheral nociceptors), nerves, and their central termination in the dorsal spinal cord. Preferably, the NMDA receptors are located at the central presynaptic terminations of sensory neurons and at postsynaptic sites in spinal cord and brain. Although the present invention includes all subjects, mammals are preferred, with humans being particularly preferred.

Although d-methadone is preferred, other substances that block the NMDA receptor and, as such, are useful in the practice of the present invention are the d-isomers of analogs of d-methadone, such as d-methadol, d-alpha-acetylmethadol, and d-alpha-normethadol, mixtures thereof, and pharmaceutically acceptable salts thereof. In addition, l-isomers of analogs of methadone, such as l-alpha-acetylmethadol and l-alpha-normethadol, mixtures thereof, and pharmaceutically acceptable salts thereof are useful in the practice of the present invention.

The NMDA receptor plays an important role in pain transmission by modulating both "wind-up," a physiological phenomenon whereby spinal cord neurons become abnormally active after repetitive C-fiber stimulation (Dickenson, et al., "Evidence for a Role of the NMDA Receptor in the Frequency Dependent Potentiation of Deep Rat Dorsal Horn Nociceptive Neurones Following C Fibre Stimulation," Neuropharmacology, 26:1235–38 (1987), which is hereby incorporated by reference), and central sensitization, the more general phenomenon whereby sensory neurons decrease activation thresholds, enlarge receptive field size, and fire spontaneously in the aftermath of noxious peripheral stimulation (Woolf, et al., "The Induction and Maintenance of Central Sensitization is Dependent on N-methyl-D-aspartic Acid Receptor Activation; Implications for the Treatment of Post-Injury Pain Hypersensitivity States," Pain, 44:293–99 (1991); Dubner, et al., "Activity-Dependent Neuronal Plasticity Following Tissue Injury and Inflammation," Trends Neurosci., 15:96–103 (1992), which are hereby incorporated by reference). Blockage of the NMDA receptor with an NMDA receptor antagonist produces antinociception in a variety of animal pain models. Thus, d-methadone, although it has little opioid activity, is antinociceptive, because it possesses in vivo NMDA receptor antagonist activity. Further, d-methadone contributes to the analgesic effects of other analgesic drugs.

Activation of the NMDA receptor, a subtype of excitatory amino acid receptors, induces a number of changes in the functional activity of nerve cells, and in particular, their capacity for excitability or inhibition in the presence of an addictive substance, via an increase in intracellular Ca++ concentration. The major consequences of NMDA receptor activation include the following sequences, or cascades, of events occurring within nerve cells:

a) translocation and activation of protein kinases such as protein kinase C→phosphorylation of substrate proteins, such as cytosolic enzymes, channel proteins, receptor proteins, etc.→changes in functional activity;

b) initiation of early gene (c-fos, c-jun, zif-268, etc.) expression by either increased intracellular Ca++ or Ca++-activated protein kinases→expression of functional genes responsible for production of cellular enzymes (such as protein kinases), receptor proteins (such as the NMDA receptor), ion channel proteins (such as K+, Na+, Ca++ channels), neuropeptides (such as dynorphin), etc.→changes in functional activity;

c) Ca++/calmodulin (or other Ca++ binding proteins) induced activation of enzymes and other cellular components→activation of Ca++/calmodulin-protein kinase systems such as Ca++/calmodulin kinase II→autophosphorylation of enzymes (e.g., Ca++/calmodulin kinase II) or other functional proteins→changes in functional activity;

d) Ca++/calmodulin induced activation of constitutive nitric oxide synthase as well as induction of inducible nitric oxide synthase→production of nitric oxide→i) production of cyclic guanosine monophosphate via activation of guanosine cyclase resulting in activation of protein kinases and early gene expression; ii) direct protein modification such as enzymes, receptor and/or channel proteins; iii) lipid membrane modification and/or nucleic acid modification via scavenge of free radicals; iv) induction of neurotoxicity at higher nitric oxide levels; v) retrograde actions in adjacent neurons or glial cells such as facilitation of glutamate release/NMDA receptor activation and/or inhibition of post-synaptic NMDA receptors→changes in functional activity;

e) interactions with the cyclic adenosine monophosphate/protein kinase A system, the phospholipase C-inositol triphosphate-Ca++/diacylglycerol-protein kinase system, the phospholipase A2-arachidonic acid/-prostanoids/leukotrienes system→changes in functional activity induced by second messenger systems other than NMDA receptor/Ca++/Ca+-calmodulin/protein kinase systems; and, f) interactions with other excitatory amino acid receptor subtypes including non-NMDA receptors and metabotropic receptors as well as intracellular events subsequent to the activation of these excitatory amino acid receptor subtypes→changes in functional activity induced by the non-NMDA and the metabotropic receptor activation.

A substance that blocks the NMDA receptor will effectively prevent all of the foregoing major intracellular sequences of events from taking place. However, even with activation of the NMDA receptor, it is still possible to inhibit the development of tolerance to and/or dependence on an addictive substance by combining the addictive substance with a substance that blocks at least one of the foregoing major intracellular sequences of events. Further, it is still possible to treat pain by administering a substance that blocks at least one of the foregoing major intracellular sequences of events. Thus, e.g., a substance that interferes with translocation and activation of protein kinase C or with calmodulin induced activation of constitutive nitric oxide synthase as well as induction of inducible nitric oxide synthase is also useful for the practice of this invention.

In a method of treating pain, the d-methadone, or other d-isomers or l-isomers of analogs thereof, is administered to a subject who has pain where the d-methadone, or other d-isomers or l-isomers of analogs thereof, blocks the NMDA receptor or the intracellular consequences of N-methyl-D-aspartate receptor activation. In addition, the d-methadone, or other d-isomers or l-isomers of analogs thereof, that block the NMDA receptor or the intracellular consequences of N-methyl-D-aspartate receptor activation, can be administered in combination with another substance, such as a narcotic analgesic or other addictive substances. The d-methadone treats pain by inhibiting the development of tolerance to and/or dependence on the narcotic analgesic or addictive substance. Further, the d-methadone may be combined with other analgesics, such as adjuvant analgesics, to provide a synergistic interaction for the treatment of pain. The analgesic (narcotic or adjuvant), addictive substance, or sedative or hypnotic substances (collectively referred to herein as "analgesic drugs") is administered before, with or following the administration of d-methadone, or other d-isomers or l-isomers of analogs thereof, that block the NMDA receptor or the intracellular consequences of N-methyl-D-aspartate receptor activation.

The types of "analgesic drugs" are described as follows.

Narcotic analgesics include opiates, opiate derivatives, opioids, and their pharmaceutically acceptable salts. Specific examples of narcotic analgesics include alfentanil, alphaprodine, anileridine, bezitramide, buprenorphine, butorphanol, codeine, dezocine, dihydrocodeine, diphenoxylate, ethylmorphine, fentanyl, heroin, hydrocodone, hydromorphone, isomethadone, levomethorphan, levorphanol, meptazinol, metazocine, metopon, morphine, nalbuphine, nalmefene, opium extracts, opium fluid extracts, pentazocine, propoxyphene, powdered opium, granulated opium, raw opium, tincture of opium, oxycodone, oxymorphone, pethidine(meperidine), phenazocine, piminodine, racemic methadone, racemethorphan, racemorphan, sufentanil, thebaine, tramadol, and pharmaceutically acceptable salts thereof. For a detailed discussion of these and other narcotic analgesics, reference may be made to Jaffe et al., "Opioid Analgesics and Antagonists," *Goodman and Gilman's Pharmacological Basis of Therapeutics*, Goodman et al., eds. 9th eds., Mac-Millan and Company, New York pp. 521–556 (1996) ("Jaffe"), which is hereby incorporated by reference.

Other narcotic analgesics and/or addictive substances that can be utilized herein include acetorphine, acetyldihydrocodeine, acetylmethadol, allylprodine, alphracetylmethadol, alphameprodine, alphamethadol, benzethidine, benzylmorphine, betacetylmethadol, betameprodine, betamethadol, betaprodine, clonitazene, cocaine, codeine methylbromide, codeine-N-oxide, cyprenorphine, desomorphine, dextromoramide, diampromide, diethylthiambutene, dihydromorphine, dimenoxadol, dimepheptanol, dimethylthiamubutene, dioxaphetyl butyrate, dipipanone, drotebanol, ethanol, ethylmethylthiambutene, etonitazene, etorphine, etoxeridine, furethidine, hydromorphinol, hydroxypethidine, ketobemidone, levomoramide, levophenacylmorphan, methyldesorphine, methyldihydromorphine, morpheridine, morphine methylbromide, morphine methylsulfonate, morphine-N-oxide, myrophin, nicocodeine, nicomorphine, nicotine, noracymethadol, norlevorphanol, normethadone, normorphine, norpipanone, phenadoxone, phenampromide, phenomorphan, phenoperidine, piritramide, pholcodine, proheptazoine, properidine, propiram, racemoramide, thebacon, trimeperidine and the pharmaceutically acceptable salts thereof.

Still other substances that can be utilized in the practice of the invention include the sedatives and hypnotics, e.g., benzodiazepines such as chlordiazepoxide, clorazepate, diazepam, flurazepam, halazepam, ketazolam, borazepam, oxazeparn, prazepam, temazepam, triazolam and the pharmaceutically acceptable salts thereof, barbiturates such as amobarbital, amobarbital, barbital, butabarbital, mephobarbital, methohexital, pentobarbital, phenobarbital, secobarbital, talbutal, thiamylal and thiopental and the pharmaceutically acceptable salts thereof and other sedatives and hypnotics such as chloral hydrate, meprobamate, methaqualone, methyprylon and the pharmaceutically acceptable salts thereof.

Still other analgesics and adjuvant analgesics include (1) local anesthetics including bupivacaine, lidocaine, mepivacaine, mexiletine, tocainide and others listed in "Local Anesthetics," *Goodman and Gilman's Pharmacological Basis of Therapeutics*, Goodman et al., eds. 9th eds., MacMillan and Company, New York pp. 331–347 (1996), which is hereby incorporated by reference; (2) Acetaminophen, salicylates including acetylsalicylic acid, nonsteroidal antiinflamatory drugs including propionic acid derivatives (ibuprofen, naproxen, etc), acetic acid derivatives (indomethacin, ketorolac and others), enolic acids (piroxicam and others) and cyclooxygenase II inhibitors (eg. SC-58635) and others listed in "Analgesic-antipyretic and Antiinflamatory Agents and Drugs Employed in the Treatment of Gout" *Goodman and Gilman's Pharmacological Basis of Therapeutics*, Goodman et al., eds. 9th eds., Mac-Millan and Company, New York pp. 617–657 (1996), which is hereby incorporated by reference; (3) adjuvant analgesics are used to enhance the analgesic efficacy of other analgesics (eg. opioids), to treat concurrent symptoms that exacerbate pain and provide analgesia for specific types of pain (e.g. neuropathic pain). They include corticosteroids (dexamethasone), anticonvulsants (phenytoin, carbamazepine, valproate, clonazepam and gabapentin), neuroleptics (methotrimeprazine), antidepressants (amitripline, doxepin, imipramine, trazodone), antihistamines (hydroxyzine) and psychostimulants (dextroamphetamine and methylphenidate) (Jacox A, et al. "Management of Cancer Pain. Clinical Practice Guideline No. 9", AHCPR Publication No. 94–0592. Rockville, Md. Agency for Health Care Policy and Research, U.S. Department of Health and Human Services, Public Health Service, pp 65–68 (1994), which is hereby incorporated by reference).

The present invention is directed to treating all types of pain. In particular, acute, subacute, and chronic pain is included. Specific types of chronic pain include neuropathic, somatic, and visceral pain.

Clinically, pain can be classified temporally as acute, subacute, or chronic; quantitatively as mild, moderate, or severe; physiologically as somatic, visceral, or neuropathic; and etiologically as medical or psychogenic. Acute pain (such as postoperative pain or acute traumatic pain) typically has objective signs and associated autonomic nervous system hyperactivity with tachycardia, hypertension, and diaphoresis being present. Chronic pain occurs for periods of time for three months or longer on a recurring basis. The quantitative nature (i.e. intensity) of the pain is the major factor in choosing drug therapy.

Neuropathic pain is a common variety of chronic pain. It can be defined as pain that results form an abnormal functioning of the peripheral and/or central nervous system. A critical component of this abnormal functioning is an exaggerated response of pain-related nerve cells either in the periphery or in the central nervous system. Somatic pain results from activation of peripheral receptors and somatic sensory efferent nerves, without injury to the peripheral nerve or CNS. Visceral pain results from visceral nociceptive receptors and visceral efferent nerves being activated and is characterized by deep, aching, cramping sensation often referred to cutaneous sites.

In addition, d-methadone (and the analogs, pharmaceutically acceptable salts thereof, and mixtures thereof) is useful in a method of treating narcotic addiction. Narcotic addiction is defined as when a subject has a tolerance to and a physical dependence on, and/or a physical craving for a narcotic analgesic and/or addictive substance (as described above). In the method, the d-methadone is administered to a subject having a physical dependence on, a tolerance to, and/or a craving for a narcotic analgesic or addictive substance.

The d-methadone herein may be made up in any suitable form appropriate for the desired use; e.g., oral(including immediate release and continuous release forms), rectal, parenteral (for example, subcutaneously, intravenously, intramuscularly, intraventricularly, epidurally, intrathecally), by intranasal instillation, or by application to mucous membranes, such as that of the nose, throat, and bronchial tubes, or by instillation into hollow organ walls or newly vascularized blood vessels) or topical administration, such as by way of a transdermal delivery devices, such as a patch. Suitable dosage forms for oral use include tablets, dispersible powders, granules, capsules, suspensions, syrups, and elixirs. The compounds may be administered alone or with suitable pharmaceutical diluents or carriers. Inert diluents and carriers for tablets include, for example, calcium carbonate, sodium carbonate, lactose, and talc. Tablets may also contain granulating and disintegrating agents such as starch and alginic acid, binding agents such as starch, gelatin, and acacia, and lubricating agents such as magnesium stearate, stearic acid, and talc. Tablets may be uncoated or may be coated by known techniques to delay disintegration and absorption. Inert diluents and carriers which may be used in capsules include, for example, calcium carbonate, calcium phosphate, and kaolin. Suspensions, syrups, and elixirs may contain conventional excipients, for example, methyl cellulose, tragacanth, sodium alginate; wetting agents, such as lecithin and polyoxyethylene stearate; and preservatives, e.g., ethyl-p-hydroxybenzoate.

Dosage forms suitable for parenteral administration include solutions, suspensions, dispersions, emulsions, and the like. They may also be manufactured in the form of sterile solid compositions which can be dissolved or suspended in sterile injectable medium immediately before use. They may contain suspending or dispersing agents known in the art.

The preferred dosage of analgesic drug or the d-methadone can vary widely, from about 5 to about 300 mg/day. It will be appreciated that the actual preferred amount of the d-methadone and analgesic drug to be administered according to the present invention will vary according to the particular composition formulated and the mode of administration. Many factors that may modify the action of the d-methadone can be taken into account by those skilled in the art; e.g., body weight, diet, time of administration, route of administration, rate of excretion, condition of the subject, drug combinations, and reaction sensitivities and severities. Administration can be carried out continuously or periodically within the maximum tolerated dose. Optimal administration rates for a given set of conditions can be ascertained by those skilled in the art using conventional dosage administration tests in view of the experimental data provided herein.

EXAMPLES

Example 1

To characterize further the binding properties of dl-methadone, as well as its d- and l-isomers, the ability of the different isomers of methadone to displace the noncompetitive NMDA receptor antagonist [$^3$H]MK-801 (Wong et al., "[$^3$H]MK-801 labels on Site on the N-methyl-D-aspartate Receptor Channel Complex in Rat Brain Membranes," *J. Neurochem.*, 50:274–281 (1988)) and the competitive NMDA receptor antagonist [$^3$H]CGS-19755 (Murphy et al., "Characterization of the Binding of [$^3$H]-CGS 19755: A Novel N-methyl-D-Aspartate Antagonist with Nanomolar Affinity in the Rat Brain," *Br. J. Pharmacol.*, 95:932–938 (1988), which is hereby incorporated by reference) was compared from synaptic membranes of rat forebrain and spinal cord. To determine if prototypical opioid drugs also exhibited affinity for the NMDA receptor, morphine, hydromorphone, and naltrexone, an antagonist, were studied. For the purposes of comparison, dextromethorphan, a noncompetitive NMDA receptor antagonist (Ebert et al., "Identification of a Novel NMDA Receptor in Rat Cerebellum," *Eur. J. Pharmacol., Mol. Pharmacol. Sect.*, 208:49–52 (1991); Netzer et al., "Dextromethorphan Blocks N-methyl-D-aspartate-Induced Currents and Voltage-Operated Inward Currents in Cultured Cortical Neurons," *Eur. J. Pharmacol.*, 238:209–216 (1993), which is hereby incorporated by reference), was also evaluated.

Male Sprague Dawley rats (250 to 300g) were obtained from Taconic Farms (Germantown, N.Y.). [$^3$H]MK801 (specific activity=20.3 Ci/mmole) and [$^3$H]CGS-19755 (specific activity=78.0 Ci/mmole) were obtained from New England Nuclear (Boston, Mass.). dl-Methadone, and the isomers of d-methadone [(S)-(+)- methadone HCl] and l-methadone [(R)-(−)-methadone HCl], were obtained from Lilly Research Laboratory (Indianapolis, Ind.).

Synaptic membranes were prepared from rat forebrain ("FB") (i.e. whole brain minus cerebellum and brainstem) and spinal cord ("SPCD") (i.e., lumbar-sacral section) according to procedures modified from Wong et al., "[$^3$H] MK-801 Labels on Site on the N-methyl-D-aspartate Receptor Channel Complex in Rat Brain Membranes," *J. Neurochem.*, 50:274–281 (1988), which is hereby incorporated by reference). Tissue was pooled from 4 to 6 rats and homogenized in 50 ml of ice-cold 0.32 M sucrose solution (Brinkmann Polytron (Westbury, N.Y.) homogenizer, setting 5), then centrifuged at 3,000×g for 5 minutes at 4° C. The supernatant and buffer layer were then centrifuged at 21,500×g for 15 minutes at 4° C. The $P_2$ pellet was resuspended in 5 mM ice-cold Tris HCl buffer, pH 7.4, and incubated with 0.04% Triton X at 37° C. for 20 minutes. The suspension was centrifuged at 39,000×g for 14 minutes at 4° C., and the pellet was then resuspended in ice-cold buffer, and recentrifuged at 39,000×g as described for a total of 3 times. The pellet was resuspended in 2 ml of 0.32 M sucrose solution and aliquots were frozen at −70° C. for at least 24 hours. On the day of the assay, an aliquot of membranes was thawed at room temperature, washed 4 times (39,000×g, 15 minutes at 4° C.), then the pellet was homogenized in the binding assay buffer to achieve a final concentration of 200 to 300 μg protein (forebrain) or 300 to 400 μg protein (spinal cord), as determined by Lowry et al., "Protein Measurement with Folin Phenol Reagent," *J. Biol. Chem.*, 193:265–275 (1951), which is hereby incorporated by reference, in a 250 μl total assay volume.

For forebrain, the [$^3$H]MK-801 binding assay was performed as previously described in Ebert et al., "Ketobemidone, Methadone, and Pethidine are Non-Competitive Antagonists in the Rat Cortex and Spinal Cord," *Neurosci. Lett.*, 187(3):165–168 (1995), which is hereby incorporated by reference. Triplicates of the membranes were incubated for 4 hours at room temperature in 5 mM Tris HCl/HEPES buffer, pH 7.6, containing 1 μM glycine, 50 μM l-glutamic acid, 5 nM [$^3$H]M-801, and competing drug or buffer control in a final volume of 250 μl. Non-specific binding was defined by the addition of 200 μM unlabeled MK-801. For spinal cord, the concentrations of glycine and l-glutamic acid were increased to 30 μM and 50 μM, respectively, to improve binding, and the incubation time was decreased to 2 hours. [$^3$H]CGS-19755 binding assays were conducted according to procedures modified from Murphy et al., "Characterization of the Binding of [$^3$H]-CGS 19755: A Novel N-methyl-D-aspartate Antagonist with Nanomolar Affinity in the Rat Brain," *Br. J. Pharmacol.*, 95:932–938 (1988), which is hereby incorporated by reference. Triplicates of forebrain were incubated for 50 minutes at 4° C. in 50 mM tris-HCl, pH 7.8, containing 10 nM [$^3$H]CSG-19755 and the competitor drug or buffer control in a final volume of 250 μl. Non-specific binding was defined by the addition of 100 unlabeled μM l-glutamic acid. Bound ligand as separated from free ligand by filtration using a 24 well Brandel cell harvester (Gaithersberg, Md.) followed by two washes with 2 ml of ice-cold binding buffer. The amount of ligand bound to the filter (Brandel GF/B filter paper, preincubated for 30 minutes in 0.05% polyethylenimine) was measured by use of a liquid scintillation counter after 12 hours in 5 ml of Ecoscint scintillation fluid. Specific binding was defined as the mean total cpm's bound minus mean non-specific cpm's bound. Assays were replicated 2 to 4 times. $IC_{50}$ values were determined from linear regression analysis as described in Katz, Y., et al., "Interactions Between Laudanosine, GABA, and Opioid Subtype Receptors: Implication for Laudanosine Seizure Activity," *Brain Res.*, 646:235–241 (1994), which is hereby incorporated by reference. $K_i$ values were calculated according to Cheng et al., "Relationship Between the Inhibition Constant (Ki) and the Concentration of Inhibitor which Causes 50 Percent Inhibition of an Enzymatic Reaction," *Biochem. Pharmacol.*, 22:3099–3104 (1973), which is hereby incorporated by reference.

Figure 1A:
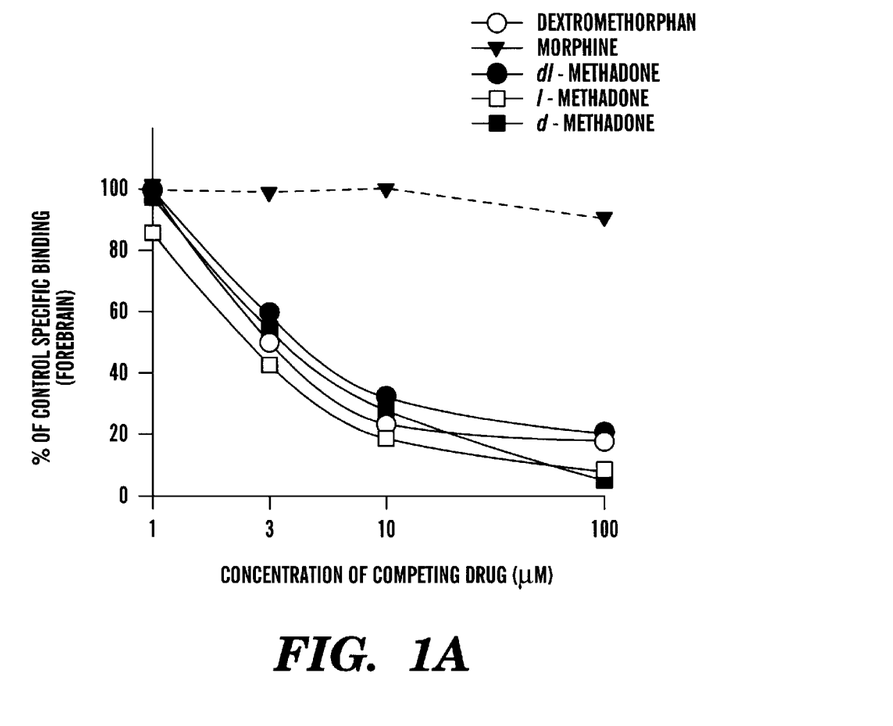
FIG. 1A is a representative curve for the displacement of 5 nM[$^3$H]MK-801 by selected opioids and dextromethorphan (1 to 100 μM) in rat forebrain membranes. Specific binding was approximately 75% of total binding.
Figure 1B:
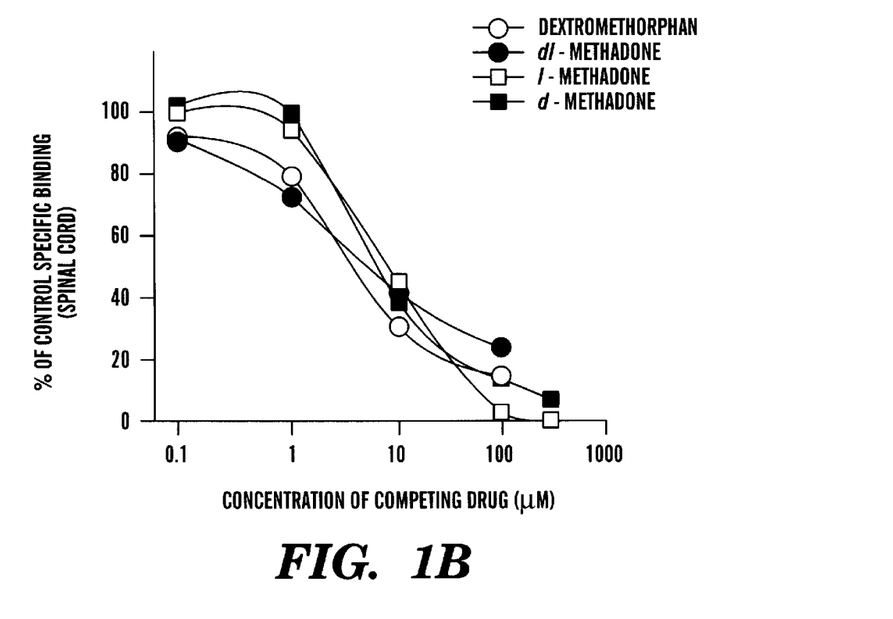
FIG. 1B is a representative curve for the displacement of 5 nM[$^3$H] MK-801 by dl-methadone, its d- and l-isomers, and dextromethorphan (0.1 to 300 μM) in rat spinal cord membranes. Specific binding was approximately 55% of total binding.

FIG. 1A shows representative curves for the displacement of [³H]MK-801 binding produced by selected opioids and dextromethorphan with forebrain. In the concentration ranges tested, morphine, hydromorphone, and naltrexone did not displace [³H]MK-801 (data are not shown for hydromorphone and naltrexone). However, dl-methadone, d-methadone, and l-methadone produced displacement curves similar to dextromethorphan, although the opioid active l-isomer appeared to be slightly more potent than its opioid inactive d-isomer or dl-methadone. FIG. 1B shows a representative displacement curve for the compounds of interest with spinal cord. Since initial assays indicated that $IC_{50}$ values were lower in spinal cord than in forebrain, lower concentrations of the compounds were tested. dl-Methadone, its d- and l-isomers, and dextromethorphan exhibited similar displacement curves.

A summary of mean $K_i$ values listed in Table 1 below, compares the ability of the compounds of interest to displace [³H]MK-801 and [³H]CGS-19755 binding.

TABLE 1

| | [³H]MK-801 $K_i$ (μM) CNS Region | | [³H]CGS-19755 $K_i$ (μM) CNS Region |
|---|---|---|---|
| Drug | Forebrain | Spinal Cord | Forebrain |
| Dextromethorphan | 5.0 ± 0.3 | 0.8 ± 0.6 | >100 |
| dl-Methadone | 8.3 ± 1.2 | 2.5 ± 0.0 | >100 |
| d-Methadone | 7.4 ± 1.2 | 2.6 ± 1.4 | >100 |
| l-Methadone | 3.4 ± 0.3 | 2.8 ± 0.9 | >100 |
| Morphine | >100 | — | — |
| Hydromorphone | >100 | — | — |
| Naltrexone | >100 | — | — |

Data are represented as mean ± SEM for 2 to 4 observations; $K_i$ was calculated from the assay $IC_{50}$ values using $K_d$ = 4.3 nM[a], $K_d$ 7.0 nM[a] (MK-801, forebrain and spinal cord, respectively), and $K_d$ = 24 nM (CGS-19755, forebrain).
—indicates that assays were not conducted,
[a] $K_d$ determined from separate saturation assays The compounds of interest displaced the competitive NMDA receptor antagonist [³H]CGS-19755 only at high concentrations (not shown). Morphine, hydromorphone, and naltrexone did not displace [³H]MK-801, and were not tested against [³H]CGS-19755. However, dl-methadone, its d- and l-isomers, and dextromethorphan exhibited moderate affinity for the noncompetitive site (MK-801) of the NMDA receptor in spinal cord and forebrain, resulting in $K_i$ values in the μM range (Table 1).

These results confirm an earlier report that dl-methadone has NMDA receptor antagonist activity in rat cortical and spinal cord membranes (Ebert et al. "Ketobemidone, Methadone, and Pethidine are Non-Competitive Antagonists in the Rat Cortex and Spinal Cord," *Neurosci. Lett.*, 187(3):165–168 (1995) ("Ebert I"), which is hereby incorporated by reference), and extend these previous results by demonstrating that both d- and l-isomers of methadone bind specifically to the noncompetitive site of the NMDA receptor in rat forebrain and spinal cord synaptic membranes. The $K_i$ value for dl-methadone is approximately 10-fold higher than previously reported in Ebert I. In this example, rat forebrain was used, while Ebert I used cortical membranes. Previously, a higher affinity for [³H]MK-801 in rat cortical membranes than in forebrain was found (Gudehithlu et al., "Effect of Morphine Tolerance and Abstinence on the Binding of [³H]MK-801 to Brain Regions and Spinal Cord of the Rat," *Brain Research*, 639:269–472 (1994), which is hereby incorporated by reference). Indeed, determined $K_i$ values for dextromethorphan were also approximately 10-fold higher in forebrain than those reported previously with cortical membranes (Ebert et al., "Identification of a Novel NMDA Receptor in Rat Cerebellum," *Eur. J. Pharmacol. Mol. Pharmacol. Sect.*, 208:49–52 (1991) ("Ebert II"), which is hereby incorporated by reference). The $K_i$ values were also 2- to 3-fold lower in spinal cord compared to forebrain. Thus, differences in the CNS regions used could account for differing $K_i$ values. Since both isomers of methadone exhibit similar affinities for the NMDA receptor, this property does not appear to be stereospecific. Further, none of the other opioids tested demonstrated affinity for the NMDA receptor, suggesting that this is not a property of the prototypical opioids.

Interestingly, the inhibition curves and $K_i$ values of dl-methadone, d-methadone, and l-methadone were similar to those of dextromethorphan, an established NMDA receptor antagonist (Ebert II; Netzer et al., "Dextromethorphan Blocks N-methyl-D-aspartate-induced Currents and Voltage-Operated Inward Currents in Cultured Cortical Neurons," *Eur. J. Pharmacol.*, 238:209–216 (1993), which are hereby incorporated by reference). Therefore, methadone may possess similar properties to dextromethorphan. Dextromethorphan attenuates nociceptive responses in the formalin test (Elliott et al., "Dextromethorphan Suppresses Formalin-Induced Nociceptive Behavior and the Formalin-Induced Increase in c-fos mRNA," *Pain*, 61:401–409 (1995), which is hereby incorporated by reference), and suppresses the "wind up" of spinal cord neurons (Dickenson et al., "Dextromethorphan and Levorphanol an Dorsal Horn Nociceptive Neurones in the Rat," *Neuropharmacology*, 30:1303–1308 (1991), which is hereby incorporated by reference), a phenomenon associated with nociceptive models of central sensitization (Coerre et al., "Contribution of Central Neuroplasticity to Pathological Pain: Review of Clinical and Experimental Evidence," *Pain*, 52:259–285 (1993), which is hereby incorporated by reference). Further, dextromethorphan attenuates and reverses the development of tolerance to morphine (Elliott et al., "Dextromethorphan Attenuates and Reverses Analgesic Tolerance to Morphine," *Pain*, 59:361–368 (1994), which is hereby incorporated by reference), a property shared by the NMDA receptor antagonists MK-801 and LY274614 (Elliott et al., "The NMDA Receptor Antagonists LY274614 and MK-801, and the Nitric Oxide Synthase Inhibitor, NG-nitro-L-arginine, Attenuate Analgesic Tolerance to the Mu-opioid Morphine but not to Kappa Opioids," *Pain*, 56:69–74 (1994), which is incorporated by reference). Since dl-methadone reduced NMDA-induced depolarizations in brain slice preparations, it exerts functional antagonism at the NMDA receptor (Ebert I). Since both the d- and l-isomers exhibits similar binding profiles to dl-methadone at the NMDA receptor, it seems reasonable to assume that the isomers also act as NMDA receptor antagonists.

These results may have some clinical implications. Compounds, like d-methadone or dextromethorphan, with NMDA receptor blocking properties that lack the tolerance and dependence producing properties of opioids may be useful adjuncts for neuropathic pain (Elliott et al. "N-methyl-D-aspartate (NMDA) Receptors Mu and Kappa Opioid Tolerance, and Perspectives on New Analgesic Drug Development," *Neuropsychopharmacology*, 13:347–356 (1995), which is hereby incorporated by reference). Additionally, the combination of morphine with an NMDA receptor antagonist, such as d-methadone, may greatly improve the efficacy or morphine by attenuating the development of morphine tolerance as has been shown for dextromethorphan (Elliott et al. "Dextromethorphan Attenuates and Reverses Analgesic Tolerance to Morphine," *Pain*, 59:361–368 (1994), which is hereby incorporated by reference).

Example 2

The l-isomer of methadone possesses opioid activity, while the d-isomer is weak or inactive as an opioid. Both d- and l-methadone have been shown to bind to the N-methyl-D-aspartate ("NMDA") receptor with a $\mu$M affinity, similar to that of dextromethorphan. To determine whether d-methadone also has functional, in vivo NMDA receptor antagonist activity, it was evaluated in the rat tail-flick and formalin tests for antinociceptive (analgesic) activity and in a morphine tolerance paradigm for its ability to attenuate analgesic tolerance. In rats prepared for intrathecal ("IT") drug administration cumulative dose-response analysis ("CDR") with the tail-flick test ("TFT") revealed an $ED_{50}$ value for IT l-methadone of 15.6 ug/rat. In contrast, IT d-methadone produced no analgesia at a cumulative dose of 460 ug/rat. However, d-methadone in a dose range from 32 to 320 ug/rat dose-dependently reduced formalin-induced flinching behavior during phase 2 but not during phase 1 of the formalin test. These analgesic effects of d-methadone were not blocked by an IT dose of naloxone that effectively antagonized an analgesic (tail-flick test) dose of l-methadone. Tolerance to the analgesic effects of IT morphine was produced by the administration, 3 times per day, of an increasing dose of morphine. d-Methadone at 160 ug/rat was coadministered with morphine and another group received d-methadone alone. On day 5, a CDR with the TFT demonstrated a 37 fold shift in the $ED_{50}$ for IT morphine in the morphine treated group as compared to the day 1 value. In contrast, the morphine $ED_{50}$ for the d-methadone+ morphine group was not significantly increased indicating that d-methadone prevented the development of morphine tolerance. d-Methadone alone did not alter the morphine $ED_{50}$ tested on day 5. These results indicate that d-methadone exerts its analgesic activity in the formalin test by a nonopioid mechanism and are consistent with the suggestion that these effects are a result of NMDA receptor antagonist activity. Furthermore, NMDA receptor antagonists have been shown to attenuate the development of morphine tolerance and a dose of d-methadone effective in the formalin test is also able to prevent the development of morphine tolerance.

Male Sprague-Dawley rats weighing 300 to 350 g were used. For the spinal administration of drugs to the rat, a catheter was placed in the intrathecal space 2 to 4 days before the experiments. Under halothane anesthesia, a PE-10 tube was inserted through a small hole made in the atlanto-occipital membrane, and threaded 9 cm down the intrathecal space to the lumbo-sacral level of the spinal cord (Shimoyama, et al., "Oral Ketamine Produces a Dose-Dependent CNS Depression in the Rat," *Life Sci.*, 60:PL9-PL14 (1997), which is hereby incorporated by reference). A catheterized rat with any signs of paralysis was excluded from the study. At the end of the study, 5 $\mu$l of a 1% methadone blue solution was introduced into the catheter followed by 10 $\mu$l of saline to confirm the position of the catheter and the spread of the dye in the intrathecal space.

The enantiomers, d-methadone [(S)-(+)-methadone] and l-methadone [(R)-(−)-methadone] were obtained from the Research Triangle Institute (Research Triangle Park, N.C.) through the Research Technology Branch of the National Institute on Drug Abuse (Rockville, Md.). The free base of each isomer was dissolved in saline with the aid of 1 N HCl to a final pH of 6.0. Naloxone hydrochloride (dose expressed as the free base) and NMDA were obtained from Research Biochemical International (Natick, Mass.). The NMDA was dissolved in saline with the aid of sodium hydroxide and the final pH was adjusted to 7.0. The naloxone and NMDA solutions were prepared alone and in a solution with d- or l-methadone, as indicated below, to limit the total volume administered.

Study 1: The antinociceptive potency of spinal d- and l-methadone were determined by the tail-flick test and cumulative dose-response analysis. Intrathecal doses of each drug were delivered in a volume of 5 $\mu$l followed by 10 $\mu$l of saline to flush the catheter. Because of the limited solubility of the isomers, the highest cumulative dose tested was 460 $\mu$g/rat. A tail-flick apparatus (EMDIE, Richmond, Va.) was used to apply radiant heat to 5 to 8 cm from the tip of the tail. The time from the onset of the heat stimulus to the withdrawal of the tail (tail-flick latency) was measured. The intensity of the radiant heat was adjusted so that the base-line latencies were between 2.5 and 3.5 seconds. Subsequent response latencies were determined at 15 minutes after spinal d- or l-methadone. This pretreatment time was selected from a time course study after 40 $\mu$g/rat of spinal l-methadone which revealed a peak analgesic effect at 15 minutes after drug administration. To avoid tissue damage, the heat stimulus was turned off after 10 seconds (cut-off latency). After measuring the base-line latencies, increasing doses of d- or l-methadone were administered until each animal became an analgesic responder (cumulative dose-response assessment, Elliott et al., "Dextromethorphan Attenuates and Reverses Analgesic Tolerance to Morphine," *Pain*, 59:361–368 (1994); Shimoyama, et al., "Ketamine Attenuates and Reverses Morphine Tolerance in Rodents," *Anesthesiology*, 85:1357–66 (1996), which is hereby incorporated by reference) or reached the highest test dose (see above). An analgesic responder was defined as one whose response tail-flick latency was 2 or more times the value of the base-line latency. The latency data were converted to a quantal form by determining the percentage of analgesic responders in each group for each cumulative dose, and a dose-response curve was constructed for each isomer of methadone. The treatment groups averaged nine animals.

Study 2: The time course of the antagonist action of spinal naloxone on the antinociceptive (tail-flick test) effects of spinal l-methadone were determined by coadminstering l-methadone at 80 $\mu$g/rat and naloxone at 30 $\mu$g/rat. Other groups received l-methadone at 80 $\mu$g/rat or naloxone at 30 $\mu$g/rat.

Study 3: To examine the effects of d-methadone on formalin-induced flinching behavior, d-methadone at a dose of 32, 160 or 320 μg/rat or saline in a volume of 10 μl was administered spinally 15 minutes before the intraplantar injection of formalin. Formalin was diluted to 5% from a stock solution of 100% (formaldehyde solution 37% w/w, Fisher Scientific Company, Fairlawn, N.J.) and was injected subcutaneously into the right hindpaw in a volume of 50 μl with the use of a 50-μl glass syringe and a new disposable 30-gauge needle. Immediately after the formalin injection, the rat was placed in a test chamber and was observed continuously by a blinded observer for the next 60 minutes. The number of flinches, defined as quick shakes of the injected hindpaw, were recorded. The formalin injection resulted in a biphasic reaction of flinching behaviors (phase 1, 0–10 minutes; phase 2, 10–60 minutes). Each rat was observed for overt central nervous system behavioral effects throughout the experiment and tested for its ability to negotiate a 60-degree mesh (Shimoyama, et al., "Oral Ketamine in Antinociceptive in the Rat Formalin Test (abstract)," 8th *World Congress on Pain*, 62:129 (1996), which is hereby incorporated by reference) immediately before the injection of formalin.

Study 4: The effects of spinal d-methadone on the formalin test were evaluated with or without the concurrent administration of naloxone. Naloxone at a dose of 30 μg/rat completely blocked the effects of an approximately $ED_{90}$ antinociceptive dose of spinal l-methadone (80 μg/rat) on the tail-flick test for at least 75 minutes (see FIG. 2). Saline, d-methadone at 250 μg/rat or d-methadone at 250 μg/rat+ naloxone 30 μg/rat was administered spinally to rats 15 minutes before intraplantar formalin, and the formalin-induced flinching behavior was observed by a blinded observer as in study 3.

Study 5: The ability of spinal d-methadone to antagonize the nociceptive behavioral responses to intrathecal NMDA was determined by estimating the $ED_{50}$ values for NMDA-induced behaviors after pretreatment with saline or d-methadone at 250 μg/rat. Spinal NMDA produces a short-lasting behavioral response which consists of intense caudally directed biting, licking, and scratching behaviors that are usually accompanied by vocalization (Okano, et al., "Pharmacological Evidence for Involvement of Excitatory Amino Acids in Aversive Responses Induced by Intrathecal Substance P in Rats," *Biol. Pharm. Bull.* (*Japan*), 16:861–65 (1993), which is hereby incorporated by reference). Doses of NMDA from 0.6 to 7.3 nmol/rat were administered intrathecally with a 3-minute interinjection interval. A responder was defined as a rat in which NMDA produced a scratching, biting, and licking of the caudal dermatomes that was at least 30 seconds in duration. Once an animal became a responder, it was not subjected to further testing.

Statistical analysis: The quantal dose-response data in Study 1 were analyzed with the BLISS-21 computer program (Oxford University, Oxford, England). This program maximized the log-likelihood function to fit a gaussian normal sigmoid curve to the dose-response data and provided the $ED_{50}$ value and a 95% confidence interval ("CI") (Umans, et al., "Pharmacodynamics of Subcutaneously Administered Diacetylmorphine, 6-acetylmorphine and Morphine in Mice," *J. Pharmacol. Exp. Ther.*, 218:409–15 (1981), which is hereby incorporated by reference). The formalin test data in studies 3 and 4 were analyzed by a one-way analysis of variance and the Student's t test, respectively. Statistical significance was accepted at P>0.05.

Results

Figure 2:
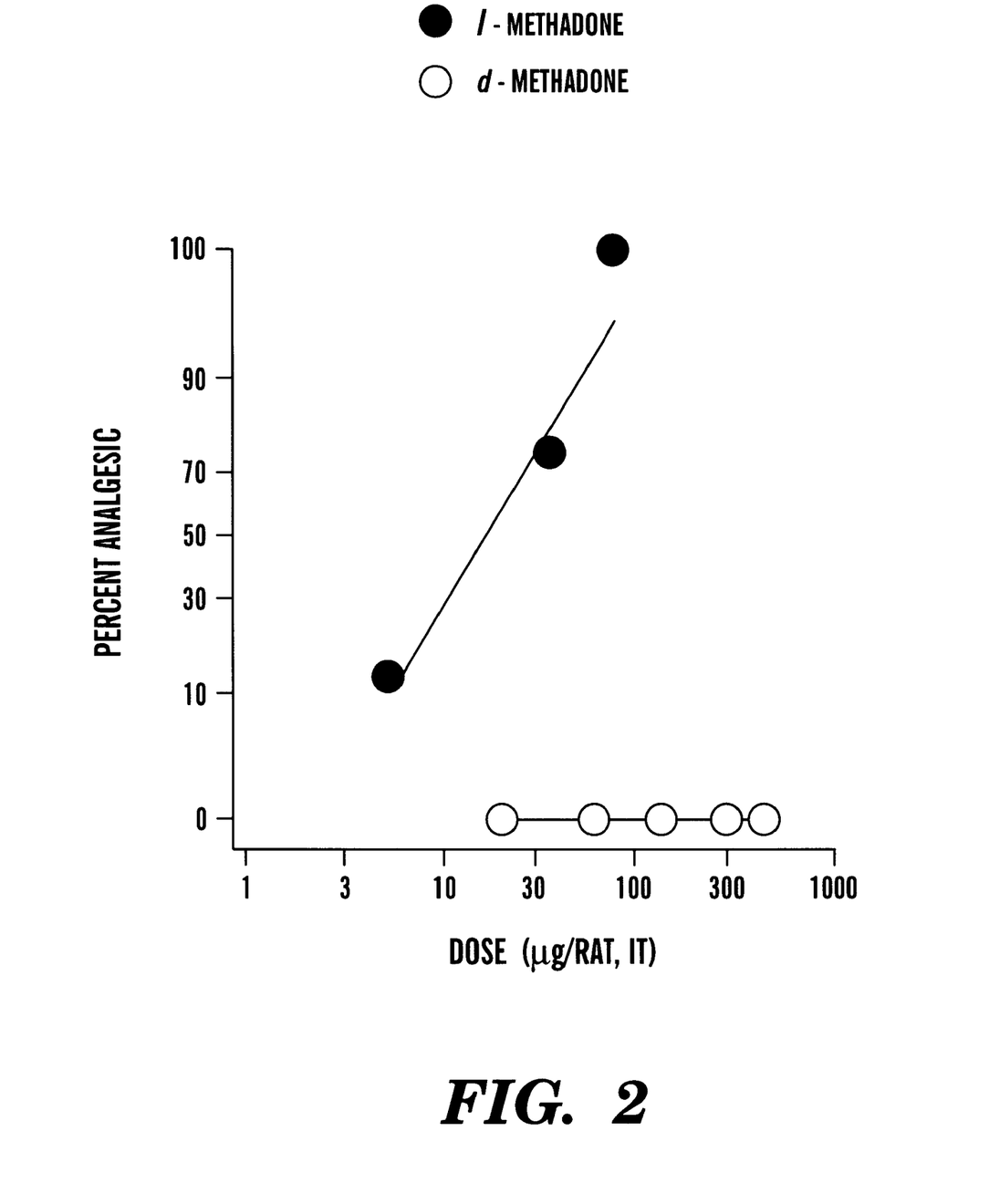
FIG. 2 shows a dose-response curve for intrathecal ("IT") l- and d-methadone in the rat tail-flick test. l-Methadone produced dose-dependent antinociception (analgesia) with a $ED_{50}$ value of 15.6 μg/rat (7.0–29.8 μg, 95% Cl). d-Methadone produced no antinociceptive effects at doses that ranged from 20 to 460 μg/rat.

Study 1: Effects of d- and l-methadone on the tail-flick test. FIG. 2 compares the antinociceptive activity of l- and d-methadone as a function of the spinal dose. l-Methadone produced dose-dependent antinociception and the analysis yielded an $ED_{50}$ value for spinal l-methadone of 15.6 μg/rat (7.0–29.8 μg/rat, 95%CI). None of the rats that received d-methadone became an analgesic responder at a cumulative spinal dose of 460 μg/rat, which was the highest dose administered.

Figure 3:
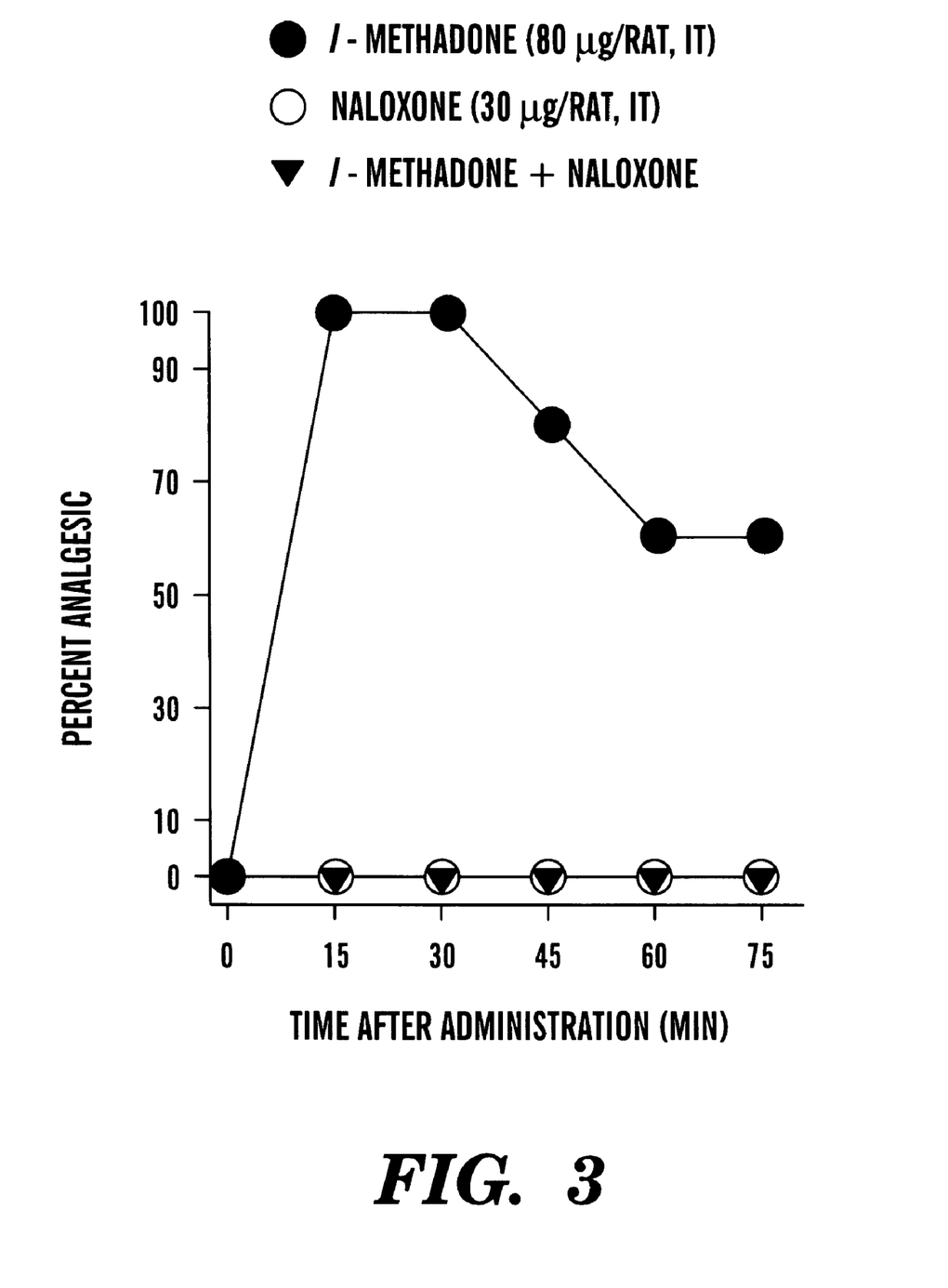
FIG. 3 shows that naloxone blocks the antinociceptive (analgesic) effects of intrathecal ("IT") l-methadone in the rat tail-flick test. l-Methadone at 80 μg/rat, l-methadone at 80 μg/rat+naloxone at 30 μg/rat, or naloxone at 30 μg/rat were administered (IT) to rats and tail-flick latencies were measured before and at 15, 30, 45, 60, and 75 minutes after drug administration. The percentage of analgesic responders were determined for each group.

Study 2: Naloxone prevents the effect of l-methadone on tail-flick latency. Spinal naloxone at 30 μg/rat did not affect base-line tail-flick latencies or produce an antinociceptive (analgesic) response (FIG. 2). However, this dose of spinal naloxone completely blocked the antinociceptive effects of an 80 μg/rat dose of l-methadone from 15 to 75 minutes after drug administration (FIG. 3).

Study 3: Effects of d-methadone on the formalin test. Spinal d-methadone at 32 μg/rat did not produce any overt central nervous system effects and each rat given this dose was able to negotiate the 60-degree mesh immediately before the injection of formalin. Spinal d-methadone at 160 and 320 μg/rat produced transient motor paralysis of the hind limbs in 44% and 100% of the rats, respectively. The onset of the paralysis was approximately 1 minute after the administration of d-methadone and lasted 30 seconds to 7 minutes. However, by the initiation of the formalin test, each rat had recovered from the paralysis and was able to negotiate the 60-degree mesh. Similar motor effects have been observed after the administration of a large spinal dose of the NMDA receptor antagonist, ketamine, to rats (Chaplan, et al., "Efficacy of Spinal NMDA Receptor Antagonism in Formalin Hyperalgesia and Nerve Injury Evoked Allodynia in the Rat," *J. Pharmacol. Exp. Ther.*, 280:829–38 (1997), which is hereby incorporated by reference). These effects were very rapid in onset, which resembled the motor effects of a local anesthetic, and resolved rapidly, probably as a result of the dilution of the drug in spinal CSF.

Figure 4A:
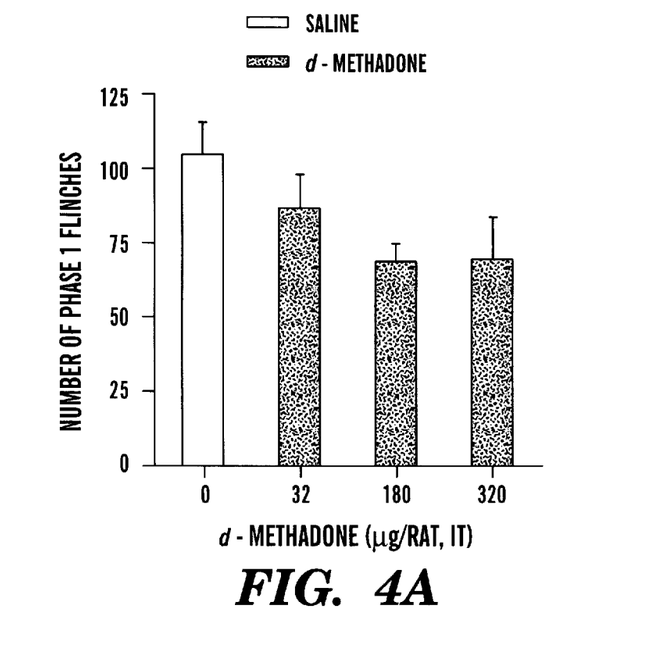
FIG. 4A shows the number of flinches (mean+S.E.M.) observed during phase 1 (0–10 minutes after formalin)
Figure 4B:
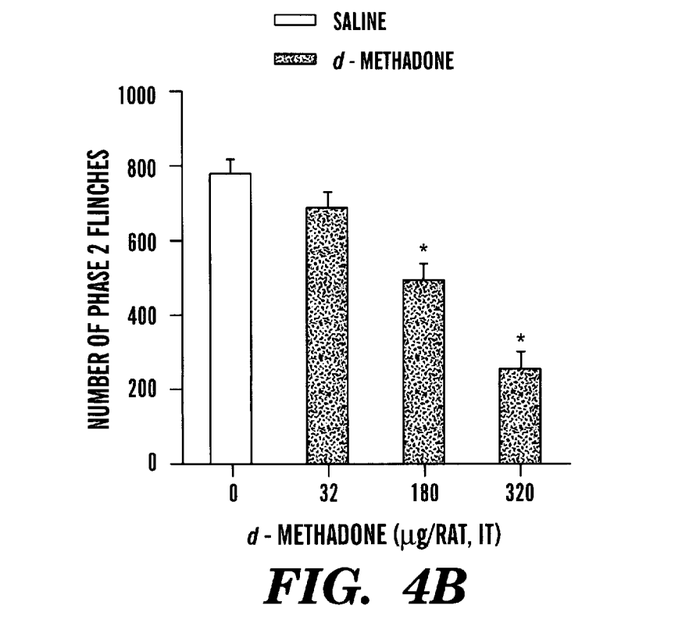
FIG. 4B shows the number of flinches (mean+S.E.M.) observed during phase 2 (10–60 minutes after formalin). *Significantly different (P<0.05) from the saline (0 μg) treatment group.

Spinal d-methadone did not affect the number of flinches during phase 1 (FIG. 4A), but dose-dependently reduced the phase 2 flinching behavior, with the 320 μg/rat dose producing a 68% decrease in flinching (FIG. 4B).

Figure 5:
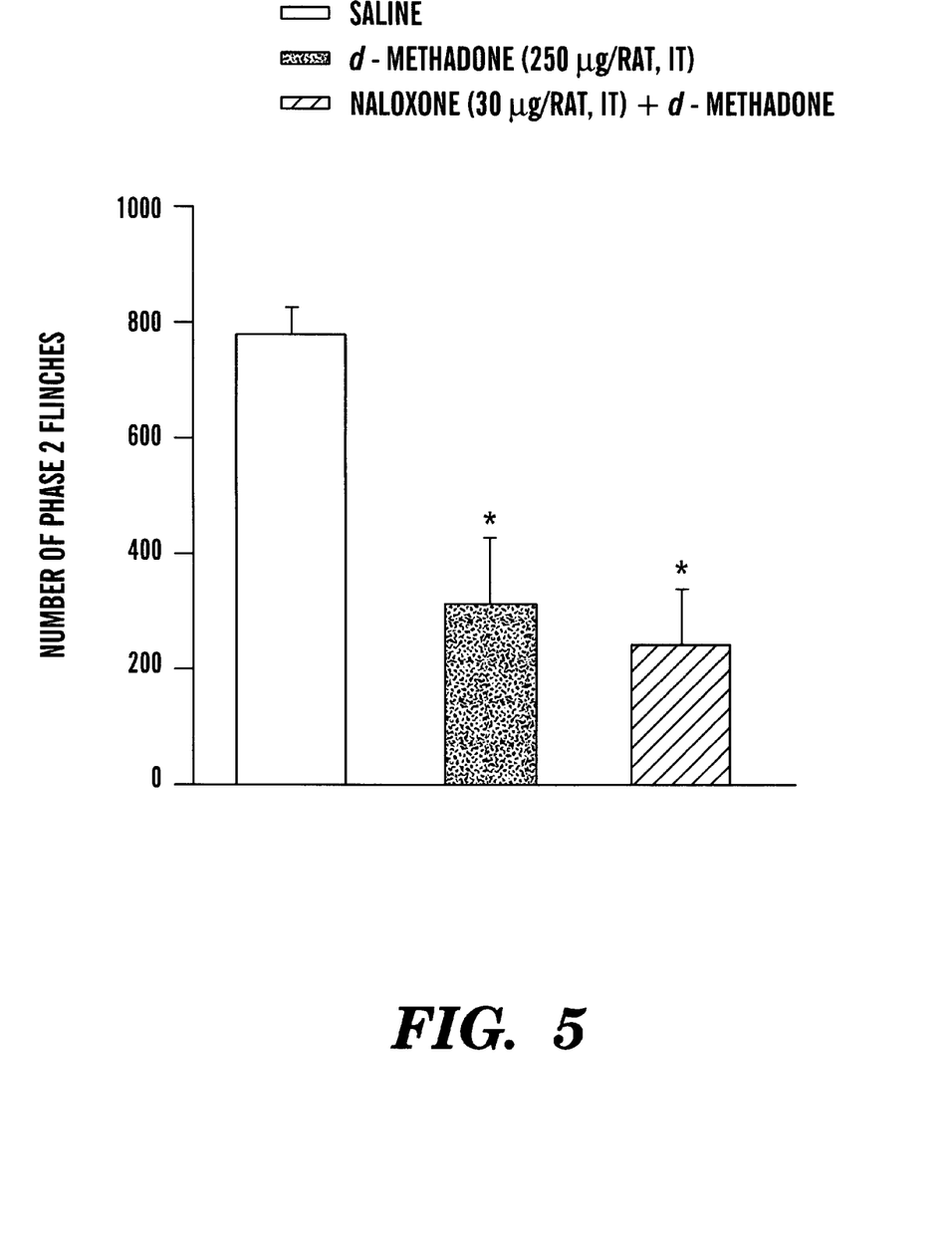
FIG. 5 shows that the antinociceptive effects of intrathecal (IT) d-methadone in the formalin test are not reversed by naloxone. d-Methadone at 250 μg/rat was administered IT with or without the concurrent administration of naloxone at 30 μg/rat, 15 minutes before the intraplantar injection of formalin. No difference was observed between the two drug-treated groups in the number of flinches occurring during phase 2. Both drug-treated groups were significantly different (*P<0.05) from the saline treatment group.

Study 4: Effects of naloxone on the antinociceptive effects of d-methadone in the formalin test. The coadministration of spinal naloxone at 30 μg/rat did not affect the ability of spinal d-methadone at 250 μg/rat to significantly reduce phase 2 flinching compared with spinal saline in the formalin test (FIG. 5). There was no statistical difference in the number of phase 2 flinches between the two drug-treated groups (FIG. 5).

Study 5: Antagonism by d-methadone of the nociceptive behavioral effects of NMDA. Pretreatment with d-methadone at a dose of 250 μg (809 nmol)/rat completely blocked an $ED_{99}$ dose (2.4 nmol/rat) of NMDA. This dose of d-methadone shifted the NMDA dose-response curve to the right, so that the $ED_{50}$ value for NMDA was increased more than 3-fold as shown in Table 2 below (Table 2).

TABLE 2

| Treatment | NMDA $ED_{50}$ (nmol/rat IT) | (95% CI) | Relative Potency |
| --- | --- | --- | --- |
| Saline + NMDA | 1.3 | (1.0–1.6) | 1.00 |
| d-Methadone + NMDA | 4.3* | (3.4–5.0) | 0.30 |

*Significantly different (p < .05) from the Saline + NMDA group.

Discussion

Abundant evidence suggests that NMDA receptors are involved in the nociceptive responses to formalin. Pretreatment with a competitive NMDA receptor antagonist [e.g., APV[3-amino-5-phosphonovaleric acid] or a noncompetitive NMDA receptor antagonist {e.g., MK-801, [(+)-5 methyl-10,11-dihydro-5H-dibenzo[a,d]cyclo- hepten -5, 10-imine hydrogen maleate], dextromethorphan or ketamine} reduces nociceptive behavioral and/or electrophysicological responses induced by formalin (Coderre, et al., "The Contribution of Excitatory Amino Acids to Central Sensitization and Persistent Nociception After Formalin-Induced Tissue Injury," *J. Neurosci.*, 12:3665–70) (1992); Haley, et al., "Evidence for Spinal N-methyl-D-aspartate Receptor Involvement in Prolonged Chemical Nociception in the Rat," *Brain Res.*, 518:218–26 (1990); Yamamoto, et al., "Comparison of the Antinociceptive Effects of Pre- and Posttreatrnent with Intrathecal Morphine and MK801, an NMDA Antagonist, on the Formalin Test in the Rat," *Anesthesiology*, 77:757–63 (1992); Vaccarino, et al., "NMDA Receptor Antagonists, MK-801 and ACEA-1011, Prevent the Development of Tonic Pain Following Subcutaneous Formalin," *Brain Res.*, 615:331–34 (1993); Hunter, et al., "Role of Excitatory Amino Acid Receptors in the Mediation of the Nociceptive Response to Formalin in the Rat," *Neurosci. Lett.*, 174:217–21 (1994); Elliott, et al., "Dextromethorphan Attenuates and Reverses Analgesic Tolerance to Morphine," *Pain*, 59:361–68 (1995); Shimoyama, et al., "Ketamine Attenuates and Reverses Morphine Tolerance in Rodents," *Anesthesiology*, 85:1357–66 (1996), which are hereby incorporated by reference). The effects of NMDA receptor antagonists are primarily on phase 2 behaviors of the formalin response (Coderre, et al., "The Contribution of Excitatory Amino Acids to Central Sensitization and Persistent Nociception After Formalin-Induced Tissue Injury," *J. Neurosci*, 12:3665–70 (1992), which is hereby incorporated by reference). Phase 2 of the formalin test appears to reflect central sensitization. The barrage of C-fiber inputs produced by formalin most likely activates spinal cord NMDA receptors, which results in the sensitization of dorsal horn neurons. This results in the amplification of the response of the dorsal horn neuron to the C-fiber inputs. These C-fiber inputs continue throughout the period of behavioral nociceptive responses (McCall, et al., "Formalin Induces Biphasic Activity in C-Fibers in the Rat," *Neurosci. Lett.*, 208:45–8 (1996), which is hereby incorporated by reference). NMDA antagonists, by blocking the activation of the NMDA receptors, prevent sensitization of dorsal horn neurons and thereby reduce the behavioral nociceptive responses to formalin. NMDA receptor antagonists alter tail-flick latencies only at doses significantly higher than those required to affect the formalin test (Nasstrom, et al., "Antinociceptive Actions of Different Classes of Excitatory Amino Acid Receptor Antagonists in Mice," *Eur. J. Pharmacol.*, 212:21–9 (1992); Elliott, et al., "Dextromethorphan Attenuates and Reverses Analgesic Tolerance to Morphine," *Pain*, 59:361–68 (1995), which is hereby incorporated by reference).

A more direct assessment of the NMDA receptor antagonist activity of d-methadone is provided by its ability to antagonize NMDA-induced nociceptive behaviors. NMDA, when localized to the spinal cord of the rat, produces dose-dependent, nociceptive behaviors that are antagonized by APV, an NMDA receptor antagonist, but not by a non-NMDA or an NK-1 receptor antagonist (Okano, et al., "Pharmacological Evidence for Involvement of Excitatory Amino Acids in Aversive Responses Induced by Intrathecal Substance P in Rats," *Biol. Pharm. Bull. (Japan)*, 16:861–65 (1993), which is hereby incorporated by reference). Table 2 demonstrates that the same dose of d-methadone that is effective in the formalin test (FIG. 4) is also able to antagonize the nociceptive effects of NMDA.

The tail-flick test is an opioid-sensitive test and has been used extensively to evaluate the analgesic effects of opioids (Székely, J., "The Most Characteristic In Vivo Effects of Opiates," In *Opioid Peptides*, ed. by J. I. Székeley and A. Z. Ronai, pp. 29–109, CRC Press, Boca Raton, Fla. (1982), which is hereby incorporated by reference). Opioid agonists such as morphine are effective in suppressing acute nociceptive responses such as those produced in the tail-flick assay as well as the nociceptive responses produced during phases 1 and 2 of the formalin test (Yaksh, et al., "Central Pharmacology of Nociceptive Transmission," In *The Textbook of Pain*, ed. by P. D. Wall and R. Melzack, pp. 165–200, Churchill Livingstone, London (1994), which is hereby incorporated by reference). The activity or lack of activity of a drug, as a function of dose, in the tail-flick test (FIG. 2) and in the formalin test (FIG. 4, A and B) as well as the ability of the opioid antagonist, naloxone, to block (FIG. 3) or fail to block (FIG. 5) an antinociceptive effect can be used to determine whether a drug is acting primarily by an opioid or a nonopioid mechanism. Clearly d-methadone appears to act as a nonopioid in the assays conducted in this study. Furthermore, the ability of a nonopioid drug such as d-methadone to affect phase 2 but not phase 1 of the formalin test (FIG. 4, A and B) and to antagonize NMDA-induced nociceptive behaviors (Table 2), when taken together with the demonstration that d-methadone is a noncompetitive NMDA receptor antagonist in vitro (Gorman, et al., "The d- and l-Isomers of Methadone Bind to the Non-Competitive Site on the N-methyl-D-aspartate (NMDA) Receptor in Rat Forebrain and Spinal Cord," *Neurosci. Lett.*, 223:5–8 (1997), which is hereby incorporated by reference), strongly suggests that d-methadone is antinociceptive in vivo by virtue of its NMDA receptor antagonist activity.

Thus, the clinically available racemic methadone may possess in vivo NMDA receptor antagonist activity in addition to its well-established opioid agonist activity. NMDA receptor antagonists have potentiated the antinociceptive effects of morphine (Chapman, et al., "The Combination of NMDA Antagonism and Morphine Produces Profound Antinociceptive in the Rat Dorsal Horn," *Brain Res.*, 573:321–23 (1992); Mao, et al., "Oral Adrninistration of Dextromethorphan Prevents the Development of Morphine Tolerance and Dependence in Rats," *Pain*, 67:361–68 (1996), which are hereby incorporated by reference). Thus, the NMDA receptor antagonist activity of the d-isomer of methadone may potentiate the opioid antinociceptive effects of l-methadone. In addition, NMDA receptor antagonists attenuate the development of morphine tolerance (Tiseo, et al., "Attenuation and Reversal of Morphine Tolerance by the Competitive N-methyl-D-aspartate Receptor Antagonist, I.Y274614," *J. Pharmacol. Exp. Ther.*, 264:1090–96 (1993); Elliott, et al., "Dextromethorphan Attenuates and Reverses Analgesic Tolerance to Morphine," *Pain*, 59:361–68 (1995); Shimoyama, et al., "Ketamine Attenuates and Reverses Morphine Tolerance in Rodents," *Anesthesiology*, 85:1357–66 (1996), which are hereby incorporated by reference). Therefore, the NMDA receptor antagonist activity of d-methadone may act to attenuate the development of tolerance to the opioid component of racemic methadone. Clinically, NMDA receptor antagonists are effective in the treatment of neuropathic pain syndromes (Backonja, et al., "Response of Chronic Neuropathic Pain Syndrome to Ketamine: A Preliminary Study," *Pain*, 56:51–7 (1994); Eide, et al., "Relief of Post-Herpetic Neuralgia with the N-methyl-D-aspartic Acid Receptor Antagonist Ketamine: A Double-Blind, Cross-Over Comparison with Morphine and Placebo," *Pain*, 58:347–54 (1994); Max, et al., "Intravenous Infusion of the NMDA Antagonist, Ketamine, in Chronic Posttraumatic Pain with Allodynia: A Double-Blind Comparison to Alfentanil and Placebo," *Clin. Neuropharmacol.*, 18:360–68 (1995), which are hereby incorporated by reference) which may often be less responsive to opioid such as morphine. Thus, as a result of its NMDA receptor antagonist activity, racemic methadone may have antinociceptive actions that are different from other mu opioids such as morphine or hydromorphone which do not bind to NMDA receptors (Gorman, et al., "The d- and l-Isomers of Methadone Bind to the Non-Competitive Site on the N-methyl-D-aspartate (NMDA) Receptor in Rat Forebrain and Spinal Cord," *Neurosci. Lett.*, 223:5–8 (1997), which is hereby incorporated by reference). Anecdotal case reports have suggested the successful management with methadone of pain syndromes that were unresponsive to morphine (Leng, et al., "Successful Use of Methadone in Nociceptive Cancer Pain Unresponsive to Morphine," *Palliative Med.*, 8:153–55 (1994); Gardner-Nix, J. S., "Oral Methadone for Managing Chronic Nonmalignant Pain," *J. Pain Symptom Manage.*, 11:321–28 (1996), which are hereby incorporated by reference).

In conclusion, spinal d-methadone is antinociceptive in the rat formalin test and antagonizes NMDA-induced nociceptive behaviors. This in vivo activity appears to be the result of NMDA receptor antagonist activity. The extent to which this activity affects the pharmacology of racemic methadone remains to be determined.

Example 3

Tolerance to the analgesic effects of IT morphine was produced by the administration, 3 times per day, of an increasing dose of morphine (10 ug/rat IT on day 1, 20 ug/rat on day 2, and 40 ug/rat on day 3). Other rats received d-methadone (160 ug/rat) and escalating doses of morphine or d-methadone+saline. On days 1 and 5, cumulative morphine dose-response was used to estimate the morphine $ED_{50}$ value. On day 5, a CDR with the TFT demonstrated a high degree of tolerance, since the $ED_{50}$ for IT morphine in the morphine treated group was shifted 37 fold to the right, i.e. 37 times as much morphine was required to achieve the same analgesic effect as compared to the day 1 value. In contrast, the morphine $ED_{50}$ for the d-methadone+morphine group was not significantly increased, indicating that d-methadone prevented the development of morphine tolerance (Table 3). These results indicate that d-methadone is able to prevent the development of morphine tolerance at the same dose that blocked NMDA receptor mediated nociceptive behaviors (see Example 2). This provides strong support for the conclusion that d-methadone produces analgesia (antinociception) and blocks the development of morphine tolerance by the same mechanism.

TABLE 3

| Treatment | Day | Morphine $ED_{50}$(ug/rat) | (95% CI) |
|---|---|---|---|
| SALINE | 1 | 1.0 | (0.5–1.8) |
| SALINE + MORPHINE | 2 | 37.6 | (28.5–56.7) |
| d-METHADONE + SALINE | 5 | 3.0 | (1.4–6.5) |
| d-METHADONE + MORPHINE | 5 | 1.4 | (0.7–2.7) |

*Significantly different (p < 0.05) from each of the other 3 Groups.

Although the invention has been described in detail for the purpose of illustration, it is understood that such detail is solely for that purpose, and variations can be made therein by those skilled in the art without departing from the spirit and scope of the invention which is defined by the following claims.

What is claimed:

1. A method of treating pain in a subject having a NMDA receptor, the method comprising:

administering a substance isolated from its enantiomer and selected from the group consisting of d-methadone, d-methadol, d-alpha-acetylmethadol, l-alpha-acetylmethadol, d-alpha-normethadol, l-alpha-normethadol, pharmaceutically acceptable salts thereof, and mixtures thereof to the subject under conditions effective for the substance to bind to the NMDA receptor of the subject and thereby relieve the subject from pain.

2. The method according to claim 1, wherein the substance is d-methadone.

3. The method according to claim 2, wherein the NMDA receptor is capable of biological action, and wherein the administering is effective to block the biological action of the NMDA receptor.

4. The method according to claim 2, further comprising administering an analgesic drug to the subject in combination with the administering of d-methadone.

5. The method according to claim 4, wherein the analgesic drug is an opioid.

6. The method according to claim 4, wherein the analgesic drug is an adjuvant analgesic.

7. The method according to claim 2, wherein the subject has a central nervous system, and wherein the NMDA receptor is located in the central nervous system.

8. The method according to claim 7, wherein the subject is a mammal.

9. The method according to claim 8, wherein the mammal is a human.

10. The method according to claim 4, wherein the administering of the analgesic drug and the d-methadone is performed orally, parenterally, or topically.

11. The method according to claim 2, further comprising:

administering at least one d-isomer of an analog of d-methadone in combination with the administering of d-methadone.

12. The method according to claim 2, wherein the d-methadone in the form of a pharmaceutically acceptable salt.

13. A method of treating addiction to a narcotic or addictive substance in a subject having a NMDA receptor, the method comprising:

administering a substance isolated from its enantiomer and selected from the group consisting of d-methadone, d-methadol, d-alpha-acetylmethadol, l-alpha-acetylmethadol, d-alpha-normethadol, l-alpha-normethadol, pharmaceutically acceptable salts thereof, and mixtures thereof to the subject under conditions effective for the substance to bind to the NMDA receptor of the subject and thereby relieve the subject of addiction to the narcotic or addictive substance.

14. The method according to claim 13, wherein the substance is d-methadone.

15. The method according to claim 14, wherein the NMDA receptor is capable of biological action and wherein the administering is effective to block the biological action of the NMDA receptor.

16. The method according to claim 14, wherein the subject has a central nervous system and wherein NMDA receptor is located in the central nervous system.

17. The method according to claim 16, wherein the subject is human.

18. The method according to claim 14, wherein the administering of the d-methadone is performed orally, parenterally, or topically.

19. The method according to claim 14, further comprising:
   administering at least one d-isomer of an analog of d-methadone in combination with the administering of d-methadone.

20. The method according to claim 14, wherein the d-methadone in the form of a pharmaceutically acceptable salt.

* * * * *

UNITED STATES PATENT AND TRADEMARK OFFICE
CERTIFICATE OF CORRECTION

| | | |
|---|---|---|
| PATENT NO. | : 6,008,258 | Page 1 of 1 |
| APPLICATION NO. | : 09/010239 | |
| DATED | : December 28, 1999 | |
| INVENTOR(S) | : Charles Inturrisi | |

It is certified that error appears in the above-identified patent and that said Letters Patent is hereby corrected as shown below:

Col. 1 at lines 7-10, delete "This invention was developed with government funding under National Institute on Drug Abuse Nos. DA01457, DA07274, DA00255, and DA00198. The U.S. Government may have certain rights." and insert --This invention was made with government support under grants DA01457, DA07274, DA00255, and DA00198 awarded by National Institute on Drug Abuse. The government has certain rights in the invention-- in its place.

Signed and Sealed this

Fourteenth Day of April, 2009

JOHN DOLL
*Acting Director of the United States Patent and Trademark Office*